United States Patent [19]

Carter et al.

[11] 4,091,060
[45] May 23, 1978

[54] BALLING PROCESS

[75] Inventors: George A. Carter, Stokesley; Reginald S. Young, Uxbridge, both of England

[73] Assignee: British Steel Corporation, London, England

[21] Appl. No.: 706,593

[22] Filed: Jul. 19, 1976

[30] Foreign Application Priority Data

Jul. 29, 1975 United Kingdom ............... 31730/75

[51] Int. Cl.² ................................................ B01J 2/12
[52] U.S. Cl. .................................. 264/40.1; 264/117; 356/209; 356/210; 425/145; 425/222
[58] Field of Search ............... 264/117, 40.1; 356/209, 356/210; 425/145, 222

[56] References Cited

U.S. PATENT DOCUMENTS

| 2,720,812 | 10/1955 | Middleton | 356/210 |
| 3,277,218 | 10/1966 | Dollinger | 264/117 |
| 3,657,400 | 4/1972 | Williams | 264/117 |
| 3,817,628 | 6/1974 | Adams | 356/210 |
| 3,900,293 | 8/1975 | Sjoberg | 264/117 |

Primary Examiner—Robert F. White
Assistant Examiner—James R. Hall
Attorney, Agent, or Firm—Bacon & Thomas

[57] ABSTRACT

A process for forming balls from mineral ores, particularly iron ore, in which water is added to the ore and the balls are produced in a balling drum. The surface wetness of the balls so produced is determined by apparatus which measures the intensity of light reflected from the balls in a selected direction, and the output from the measuring apparatus is used to control the addition of water to the material fed to balling drum.

18 Claims, 5 Drawing Figures

BALLING PROCESS

This invention relates to a balling process and is concerned with the production of balls of granular material, usually in a balling drum.

The invention is particularly applicable to pelletizing in the iron and steel industry. For example, iron oxide in the form of finely ground iron ore is not fed directly to the blast furnace and pelletizing the ore is useful in the production of a suitable feed material. Pellets are formed by producing green balls from a mixture of the fine ore and water followed by drying and sintering the balls on a moving grate.

The green balls may be formed in a balling drum into which the iron ore and water are delivered in controlled proportions. Balling takes place in the rotating drum and the green balls formed are removed on a product conveyor. It is believed that an optimum water content in the compacted yet porous balls corresponds to a surface water film just being present. It is therefore considered advantageous to be able to determine when this condition is reached, or whether the balls are too dry or too wet, in which case the proportion of water fed to the material entering the balling drum can be adjusted.

According to one aspect of the present invention there is provided a process for forming balls from a feed comprising a comminuted solid and a liquid, in which the superficial liquid content of the balls is monitored by illuminating the balls with a beam of light, measuring the intensity of the light reflected in a selected direction, and controlling the addition of liquid to the comminuted solid in response to said measurements.

The liquid is preferably water.

It is preferred to take the measurements on a statistical basis, by which is meant that one or more of the following conditions are applied. The measurements are made on a plurality of balls, over a fixed period of time, in the course of which the balls are transported through the beam of light, and the frequency of reflections of different intensities occurring in the selected direction is compared with the frequency of reflections of different intensities occurring in the same direction in respect of balls of various liquids contents.

The comparison can be made in several ways. For example, it can be carried out on the basis of intensity distribution, intensity probability or maximum intensity.

According to a further aspect of the invention apparatus for determining the superficial liquid content of balls formed from a granular solid and a liquid, comprises a light source for projecting a beam of light and means for receiving and measuring the intensity of a reflected beam of light maintained in a fixed spatial relationship in which the said beams intersect at a selected angle or range of angles, and a support for balls at the intersection of the beams.

The light can be generated by any suitable means such as an incandescent lamp. The projected beam of light is preferably a collimated beam. The width of the beam as it strikes the balls is preferably significantly larger than the diameter of the balls. Illustratively, beams of a width greater than about ten times the average ball diameter would be preferred in this context. It is preferred to avoid projecting beams of a width either similar to or much less than the ball diameters because beams of such widths are less reliable for relating the intensities of the reflected beams to the liquid content of the balls.

In a preferred form of the invention the support for the balls at the intersection of the beams is a moving conveyor. The beam may be projected onto the balls on the conveyor shortly after the balls have been formed.

Means may also be provided for comparing the measured intensities with intensities determined in respect of balls of various liquid contents, and this comparison will normally be made by the operator from data presented fo him.

The reflected light may be received by a photodiode. The output of the photodiode may be used in conjunction with a counting device to provide a numerical signal which may be used by the operator for controlling the wetness of the balls. Alternatively, the photodiode and its associated counting device may be used to produce a signal which controls the relative addition of liquid to the material used in the formation of the balls.

One embodiment of the invention will now be described by way of example with reference to the accompanying drawings in which.

Figure 1:
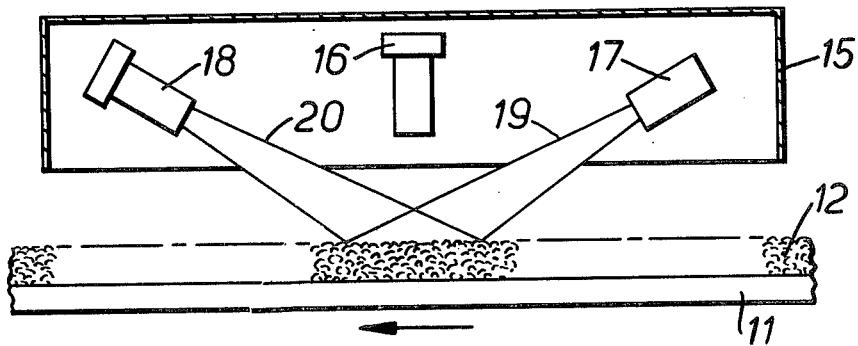
FIG. 1 is a simplified elevation of a product conveyor, situated immediately after a balling drum, adapted in accordance with the invention.

In FIG. 1 a conveyor 11 moves in the direction of the arrow. It carries green balls 12 of iron oxide, water, adhesives and additives. The balls have been formed in a balling drum (FIG. 5) from which they have been discharged immediately before the conveyor.

The conveyor carries the balls closely under a hood 15 in the form of an open-bottomed but otherwise light-tight box. The hood contains in fixed positions and orientations an ambient light sensor 16, an incandescent light source 17 and a reflected beam detector 18.

The light source 17 projects a beam of light 19 on to an area of the conveyor covered by green balls. The detector 18 is aligned with that area and will accept light 20 reflected from it. The ambient light sensor 16 is also broadly directed towards that area and detects light emanating from it. The light beam 20 reflected from the green balls towards the detector 18 is made up of intermittent individual reflections in the correct direction from individual ball surfaces.

The angle through which the light is reflected is one chosen by experiment to suit the particular installation. The angle is not a precise single value because of the divergence of the beam 19 and the convergence of the beam 20. In the example shown in FIG. 1 the angle between the two beams is around 120°.

We have found that an angle less than 90° results in insufficient reflection for useful results. Advantage is taken of this to use the ambient light sensor 16, which is positioned directly above the illuminated green balls so that the angle between the beam it accepts and the incident beam 20 is about 60°. Thus it effectively registers only the background light level, since light it detects due to the light source 17 is insignificant. On the assumption that the detector 18 is influenced by approximately the same background light level, intensity measurements are based on the difference between the light measured at 18 and 16.

In the absence of the hood 15 or alternative light screen it would be particularly desirable to use an ambient light sensor in this way.

Figure 2:
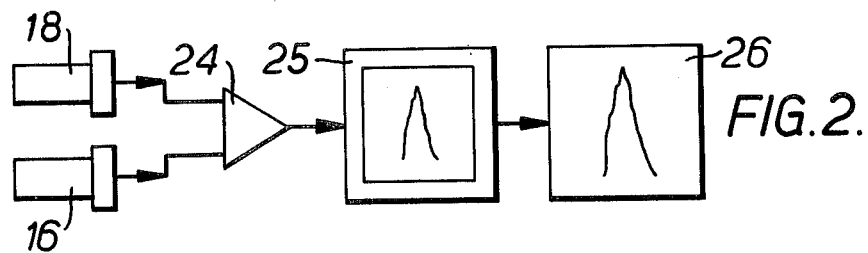
FIG. 2 is a diagrammatic representation of stages in the processing of measurements of the intensity of light reflected from green balls on the product conveyor.

FIG. 2 also shows the ambient light sensor 16 and the detector 18, each of which comprises a lens system and a photocell on to which the incident light beam is focussed. The buffered outputs from the two photocells are taken to differential amplifier 24 which gives a continuously changing signal, the level of which is a measure of the changing intensity of light reflected by the green balls through the selected angle.

The signal is fed to a correlator 25 operating in the amplitude sampling analysis mode to build up over a period of time a frequency of probability distribution for the photocell output. This is displayed and recorded at a plotter 26.

Figure 3:
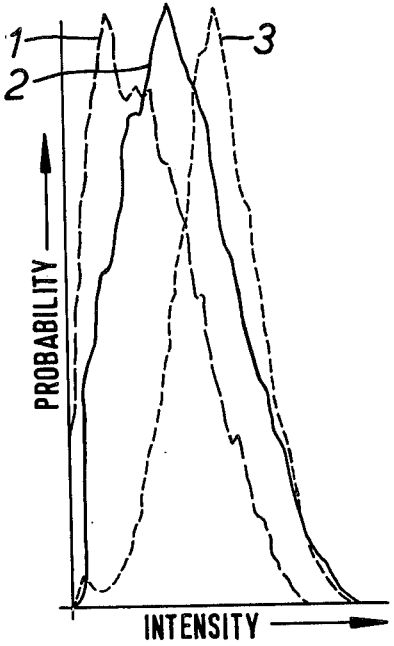
FIG. 3 is a graph of probability against the intensity of the reflected light for three samples of green ball.

FIG. 3 shows on the same graph probability distributions built up in this manner for green balls having different surface moisture contents.

The dashed line 1 arose with balls having a lower surface water content which accordingly lacked any surface water film. These balls reflected the light in a more or less random manner corresponding to their visually dull and matt surfaces. The intensity of the reflected light tended to be low.

The dashed line 3 arose with balls having a high surface water content and the a single surface water film broken only by peaks of the solid substrate.

The continuous line 2 arose with balls of the correct median surface water content which were at the point of transition from the dull to glistening surface. Regions of continuous superficial water were just present on the green balls.

Figure 5:
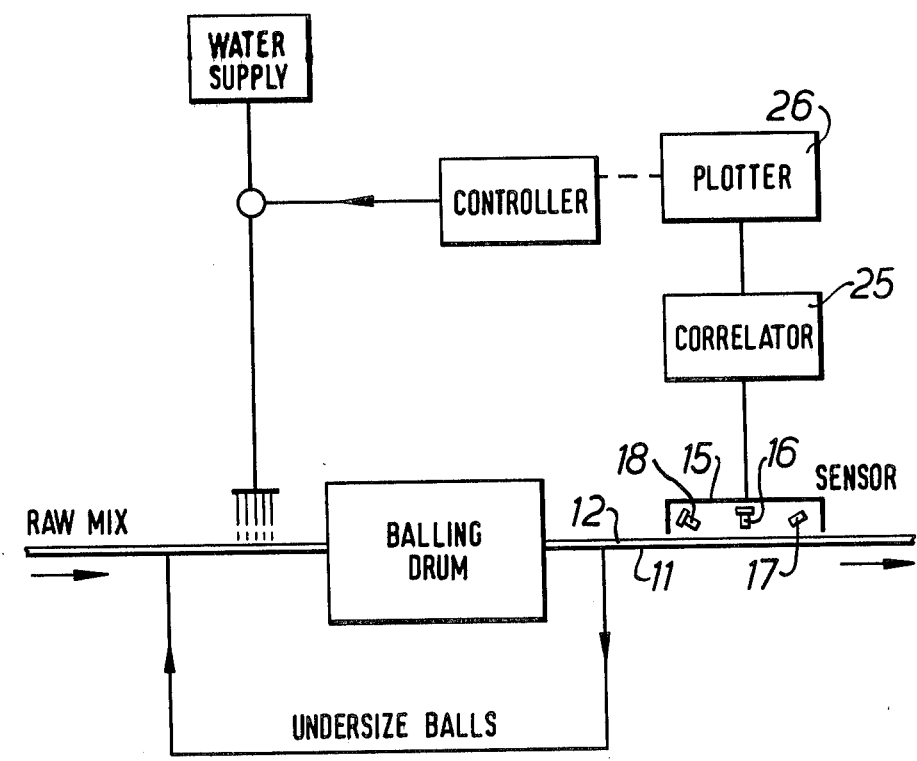
FIG. 5 is a schematic diagram of the operation of the process.

It can be seen that the three curves are quite distinct. The operator can determine by comparison with standard previously determined curves whether the balling drum product is too dry or too wet and can adjust the composition addition of water to the material entering the balling drum accordingly. This is illustrated in FIG. 5.

Figure 4:
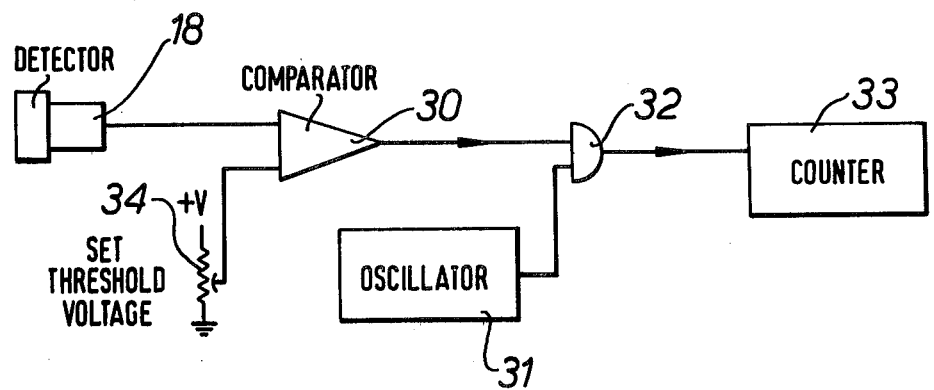
FIG. 4 is a diagrammatic representation of an alternative signal processing system to that shown in FIG. 2.

Alternatively, when the detector 18 is photodiode, a voltage comparator 30 can be connected with the output from the photodiode 18 as seen in FIG. 4. The output from the comparator 30 goes 'high' if the input voltage exceeds a threshold value preset on potentiometer 34. The output from the comparator 30 gates an oscillator 31 connected to a counter 33. For a preset threshold voltage, the reading of the counter 33 accumulates over a fixed time period and is proportional to the area under the section of curve corresponding to voltages greater than the preset threshold. Thus a single numeric reading is obtained giving a qualified value of the change in reflectivity. This output can be used by the operator for controlling the wetness of the balls, or alternatively a feedback control system can be used which controls the wetness of the balls automatically.

We claim:

1. A process for continuously forming balls from communited solids, comprising:
   (a) adding a controlled amount of liquid to a moving mass of communited solids,
   (b) feeding said wetted solids into a moving balling device wherein said solids are formed into balls having a surface liquid content,
   (c) removing said formed balls from said balling device,
   (d) determining the surface liquid content of said balls by projecting upon said balls an incident light beam, and measuring the intensity of the light beam reflected from said balls in a pre-selected direction, and
   (e) controlling the amount of liquid added in step (a) in response to the determined surface liquid content of the balls as in step (d).

2. A process as claimed in claim 1 in which the liquid is water.

3. A process as claimed in claim 1 in which the comminuted solid is iron bearing.

4. A process a claimed in claim 1 in which measurements are made on a plurality of balls over a fixed period of time in the course of which the balls are transported through the beam of light.

5. A process as claimed in claim 1 in which the reflected light is received by a photodiode and the output of the photodiode is used in conjunction with a counting device to provide a numerical signal indicative of the surface liquid content of the surface of the balls.

6. A process as claimed in claim 1 in which the projected beam of light is a collimated beam.

7. A process as claimed in claim 1 in which the width of the beam as it strikes the balls is significantly greater than the diameter of the balls.

8. A process as claimed in claim 3, wherein green balls are formed of iron oxide, water, adhesives and additives.

9. A process as claimed in claim 5 in which the numerical signal produced by the counting device is used to control the relative proportion of liquid to granular solid used in the formation of the balls.

10. A process as claimed in claim 7 in which the incident light beam striking the balls having a width exceeding ten times the average ball diameter.

11. An apparatus for determining the surface liquid content of wetted balls formed from a comminuted solid and a controlled added liquid, comprising:
   (a) a light source for projecting an incident beam of light onto balls having been formed in a balling device, said balls having a surface liquid content,
   (b) means for receiving and measuring the intensity of the reflected beam of said incident light beam maintained in a fixed spacial relationship in which said beam is reflected from the surface of said formed wetted balls at a selected range of angles, and
   (c) a moving support to convey said formed balls continuously past the intersection of said projected incident light beam and said wetted formed balls.

12. Apparatus as claimed in claim 11 in which the incident beam of light is generated by an incandescent lamp.

13. Apparatus as claimed in claim 11 in which the reflected light is received by a photodiode.

14. Apparatus as claimed in claim 11, wherein an ambient light sensor is positioned above the illuminated balls.

15. Apparatus of claim 11, wherein the surface liquid detected is water amd the comminuted solid comprises iron oxide and green balls are formed.

16. Apparatus as claimed in claim 13 in which a counting device is used in conjunction with the output of the photodiode to provide a numerical signal.

17. Apparatus as claimed in claim 16 in which control means is provided to use the output from the counting device to control the relative proportion of liquid to the comminuted solid material used in the formation of the balls.

18. Apparatus as claimed in claim 14, wherein an open bottom but otherwise light tight box contains in fixed positions said incident beam projecting means, said means for receiving the reflected incident beams and said ambient light sensor.

* * * * *